United States Patent
Dalko et al.

(10) Patent No.: US 10,307,353 B2
(45) Date of Patent: Jun. 4, 2019

(54) 1-PHENYLMONO- OR -POLYHYDROXYPROPANE COMPOUNDS, COMPOSITIONS AND COSMETIC USES THEREOF

(71) Applicant: L'OREAL, Paris (FR)

(72) Inventors: Maria Dalko, Versailles (FR); Julien Hitce, Aulnay-sous-Bois (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 15/534,190

(22) PCT Filed: Dec. 11, 2015

(86) PCT No.: PCT/EP2015/079427
§ 371 (c)(1),
(2) Date: Jun. 8, 2017

(87) PCT Pub. No.: WO2016/092074
PCT Pub. Date: Jun. 16, 2016

(65) Prior Publication Data
US 2017/0360665 A1    Dec. 21, 2017

(51) Int. Cl.
| | |
|---|---|
| A61K 8/34 | (2006.01) |
| A61Q 19/08 | (2006.01) |
| C07C 43/23 | (2006.01) |
| A61K 31/085 | (2006.01) |
| A61K 31/09 | (2006.01) |

(52) U.S. Cl.
CPC .......... *A61K 8/347* (2013.01); *A61K 8/34* (2013.01); *A61K 8/345* (2013.01); *A61K 31/085* (2013.01); *A61K 31/09* (2013.01); *A61Q 19/08* (2013.01); *C07C 43/23* (2013.01)

(58) Field of Classification Search
CPC .......... A61K 8/34; A61K 8/347; A61K 8/345; A61Q 19/08
See application file for complete search history.

(56) References Cited

U.S. PATENT DOCUMENTS

2010/0184847 A1* 7/2010 Shin .............. A61K 8/498
                                                         514/452

FOREIGN PATENT DOCUMENTS

| | | | |
|---|---|---|---|
| JP | 06321746 A | * | 11/1994 |
| JP | 07300413 A | * | 11/1995 |
| JP | 2002201122 A | * | 7/2002 |
| JP | 2003 201229 A | | 7/2003 |
| KR | 20150024606 A | | 3/2015 |
| WO | WO-03/084522 A1 | | 10/2003 |
| WO | WO-2014/048868 A2 | | 4/2014 |

OTHER PUBLICATIONS

Barton, G.M. "Thin-layer chromatography of guaiacyl propane monomers, selected lignans and phenolic wood extractives" J. Chromatog., 26 (1967), 320-322 (Year: 1967).*
JP-07300413-A Machine translation, 2018, pp. 1-25 (Year: 2018).*
JP-06321746-A Machine translation, 2018, pp. 1-7 (Year: 2018).*
KR20150024606 Machine translation, 2018, pp. 1-19 (Year: 2018).*
Cho, N. et al. "Chemical constituents isolated from Disporum viridescens leaves and their inhibitory effect on nitric oxide production in BV2 microglial cells" Bioorganic & Medicinal Chemistry Letters 24 (2014) 5675-5678 (Year: 2014).*
Farage, M.A. et al. "Intrinsic and extrinsic factors in skin ageing: a review" International Journal of Cosmetic Science, 2008, 30, 87-95 (Year: 2008).*
JP-2002201122-A Derwent abstract, pp. 1-3, accessed Aug. 6, 2018 (Year: 2018).*
JP-2002201122-A machine translation. Accessed Aug. 6, 2018. pp. 1-15 (Year: 2018).*
Fan, C-Q. et al. "Biologically Active Phenols from Saussurea medusa" Bioorganic & Medicinal Chemistry 11 (2003) 703-708 (Year: 2003).*
Barton et al., "Thin-layer chromatography of gualacylpropane monomers, selected lignans and phenolic wood extractices", J Chromatog., 26 (1967) 320-322.

* cited by examiner

*Primary Examiner* — Andrew S Rosenthal
(74) *Attorney, Agent, or Firm* — Polsinelli PC

(57) ABSTRACT

The present invention relates to novel compounds of formula (I)

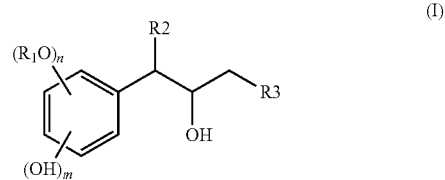

to compositions comprising same, and also to the use thereof for preventing and/or cosmetically treating the signs of aging of the skin.

14 Claims, No Drawings

1-PHENYLMONO- OR -POLYHYDROXYPROPANE COMPOUNDS, COMPOSITIONS AND COSMETIC USES THEREOF

CROSS REFERENCE TO RELATED APPLICATIONS

This application is a National Phase filing under 35 U.S.C. § 371 of PCT/EP2015/079427 filed on Dec. 11, 2015; and this application claims priority to Application No. 1462360 filed in France on Dec. 12, 2014 under 35 U.S.C. § 119. The entire contents of each application are hereby incorporated by reference.

The present invention relates to the use of 1-phenylmono- or -polyhydroxypropane derivatives for combating aging of the skin and also relates to novel 1-phenylmono- or -polyhydroxypropane derivatives, and to compositions, especially cosmetic compositions, comprising them.

Women and men currently have a tendency to wish to appear youthful for as long as possible and consequently seek to tone down the signs of aging of the skin, which are reflected especially by wrinkles and fine lines. In this regard, the advertising and fashion industries mention products for retaining radiant and wrinkle-free skin, which are signs of youthful skin, for as long as possible, all the more so since physical appearance has an effect on the psyche and/or on morale.

Hitherto, wrinkles and fine lines were treated using cosmetic products containing active agents acting on the skin, for example by improving its cell renewal or alternatively by promoting the synthesis, or preventing the degradation, of the elastic fibers which make up skin tissue.

The skin consists of two compartments, a surface compartment, the epidermis, and the other deeper compartment, the dermis, which interact. Natural human epidermis is composed mainly of three types of cells, namely keratinocytes, which form the vast majority, melanocytes and Langerhans cells. Each of these three types of cells contributes, by virtue of its intrinsic functions, to the essential role played in the body by the skin, especially the role of protecting the body against external attacking factors, which is known as the "barrier function".

The epidermis is conventionally divided into a basal layer of keratinocytes that constitutes the germinative layer of the epidermis, a spinous layer consisting of several layers of polyhedral cells positioned on the germinative layers, one to three "granular" layers consisting of flattened cells containing distinct cytoplasmic inclusions, keratohyalin granules, and finally the cornified layer (or stratum corneum), consisting of a set of layers of keratinocytes at the terminal stage of their differentiation, known as corneocytes. Corneocytes are anuclear cells mainly consisting of a fibrous material containing cytokeratins, surrounded by a cornified envelope.

The dermis provides the epidermis with a solid support. It is also its nourishing element. It consists mainly of fibroblasts and of an extracellular matrix predominantly composed of collagen, elastin and a substance, known as ground substance, comprising glycosaminoglycans that are sulfated (e.g. chondroitin sulfate) or not (e.g. hyaluronic acid), proteoglycans and various proteases. These components are synthesized by the fibroblasts. Leukocytes, mast cells or else tissue macrophages are also found therein. Finally, blood vessels and nerve fibers pass through the dermis. The cohesion between the epidermis and the dermis is provided by the dermo-epidermal junction.

The epidermis is constantly engaged in producing new keratinocytes to compensate for the continuous loss of epidermal cells at the cornified layer. However, in the course of aging, a decrease in the number of cells in the proliferation phase, and consequently a decrease of the live epidermal layers, may be observed physiologically.

The homeostasis of the skin, and in particular of the epidermis, results from a finely regulated balance between the processes of proliferation and of differentiation of the skin cells. These processes of proliferation and differentiation are entirely regulated: they participate in the renewal and/or regeneration of the skin and lead to the maintenance of a constant thickness of the skin, and in particular of a constant thickness of the epidermis. This homeostasis of the skin also participates in maintaining the mechanical properties of the skin.

However, this homeostasis of the skin may be impaired by certain physiological factors (age, menopause, hormones, etc.) or environmental factors (UV stress, oxidative stress, irritant stress, etc.).

The proliferative cells are metabolically very active and are sensitive to these deleterious factors (intrinsic or environmental), with, as a consequence on the epidermis, a reduction in their amount. Certain biochemical markers characterize this loss of regenerative capacity of the epidermis such as the Sab galactosidase activity (Dimri G P, et al. Proc Natl Acad Sci USA. 1995) or markers of impairment of the cell cycle such as p16(INK4a) (Cordisco S & al., J Invest Dermatol. 2010).

It is thus important to preserve this pool of cells in order to contribute toward delaying the onset of the signs of aging.

The cellular vitality of the keratinocytes may be decreased especially in the context of aging or on account of oxidative stress (for example solar radiation, i.e. UV, visible light, infrared), on account of attack of the epidermis by toxins or metabolites of the microflora, or, more generally, during chronological aging. The capacity for renewal and differentiation of the keratinocytes is reduced and the homeostasis of structures dependent thereon, such as the barrier function of the epidermis, is impaired.

When the regenerative potential of the epidermis becomes smaller: the cells of the basal layer divide less actively, leading especially to a slowing-down and/or decrease in epidermal renewal. Consequently, the cell renewal no longer compensates for the loss of cells removed at the surface, leading to atrophy of the epidermis and/or a reduction in skin thickness. This is likewise the case for the proliferative cells of the epidermal appendages, for example the nails, the consequence of which is a slowing-down of the growth of the nails.

The impairments in epidermal homeostasis are also reflected by a dull and/or off-color appearance of the skin complexion.

Impairment of the barrier function is manifested by various signs depending on the localization: dry skin, hyperkeratosis, thin epidermis, thin lips, surface wrinkles.

The disorders associated with impairment of the cellular vitality of the epidermis thus concern not only its structure, but also its homeostasis. The resistance to stress of the epidermis and its capacity for regeneration are reduced. If the skin barrier of an elderly person is compared with that of a young adult, the differences do not appear at first sight: the thickness of the cornified layer and the composition of its lipids are not necessarily altered, and the barrier function expressed by the transepidermal water loss is conserved. The deficiencies of the elderly skin barrier appear under mechanical stress or during exposure to irritant factors: the barrier of an elderly epidermis degrades more rapidly and its function recovers less quickly. On a daily basis, alcoholic disinfection, contact with lemon juice or other irritants then cause stinging and burning, and dry air is poorly tolerated, whereas a young skin tolerates this without any problem. An impaired skin barrier also facilitates the contact of allergens with the immune system of the epidermis, thus increasing the risk of allergic sensitization.

At the present time, there is not sufficient evidence to prove that senescent cells accumulate with age in the body. Senescence-associated β-galactosidase is a marker of senescent cells and its accumulation has been shown in vivo in the skin (Dimai G P et al Proc Nat Acad. SCI USA. 1995; 92(20): 9363-7).

Another marker of senescence is the impairment of mitochondrial functioning. The role of the mitochondrion is to produce cellular energy.

The clinical signs of the phenomenon of photoaging have been widely described (Photodermatol Photoimmunol Photomed. 2008 (4) Fourtanier A, Moyal D, Seité S.).

Intrinsic aging, also known as chronological aging, of the skin is described as a result of an impairment in cellular vitality similar to what takes place in the other organs. Intrinsic or chronological aging is manifested by other clinical markers and signs, in particular the impairment of the barrier function as described above (Farage M A et al. 2009; 10(2): 73-86).

These esthetic disorders such as dry skin, wrinkles, fine lines, etc. are such that there is a need in cosmetics for compounds acting on the skin to improve the cellular vitality when it is impaired.

AMPK is present in all the cells of the body and plays an energy gauge role therein. AMPK (or 5'-adenosine monophosphate activated protein kinase) is a heterotrimeric enzyme composed of a catalytic subunit a with kinase activity and two regulatory subunits β and γ. The activity of AMPK depends on the variation of the AMP/ATP ratio which characterizes the energy level of the cell (ATP being hydrolyzed into AMP to "deliver" the energy required for the various biochemical processes of the cell). It is present in two forms, phosphorylated or non-phosphorylated, the phosphorylated form being the active form.

When it is activated in response to an energy demand or a stress of the cell, AMPK increases the energy-generating processes such as glycolysis and it inhibits the non-essential consuming processes, thus enabling cell survival. Preservation of the cellular energy status is involved in maintaining the longevity of the species and combating the signs of aging. Thus, compounds that are capable of increasing the activity of AMPK are at the present time the object of great interest in the treatment of age-related clinical manifestations. The value in transposing this approach, validated for the whole organism, to the skin in the context of preventing its age-related impairment may be understood.

The AMPK activity corresponds to the cellular concentration of phosphorylated AMPK. Thus, it is worthwhile having the highest possible levels of phosphorylated protein in order to have this high activity.

The role of AMPK in controlling the energy metabolism of the keratinocyte is suspected at the present time (Prahl et al., Biofactors. 2008; 32(1-4):245-55), its involvement in the proliferation and differentiation of the keratinocyte has been established (Saha A K et al. Biochem Biophys Res Commun. 2006 Oct. 20; 349(2): 519-24).

WO 2004/05098 proposes to modulate the lifetime of any cell or of an organism by controlling the activity of AMPK, and to treat age-related disorders by administering modulators of the AMPK metabolic pathway, without stating whether it involves an activator or an inhibitor.

Saha et al. (Biochem. Biophys. Res. Commun 2006, 349:519-524) studied the AMPK-regulated growth of keratinocytes and conclude that AMPK activators such as AICAR promote the in vitro differentiation of keratinocytes.

It has been found, unexpectedly, in the context of the present invention, that certain 1-phenylmono- or -polyhydroxypropane derivatives described below are capable of stimulating the activity of AMPK, in particular the production of phosphorylated AMPK by normal human keratinocytes. These compounds will thus be particularly useful for combating the decrease in the vitality of skin cells during aging, and retarding the onset of the signs associated therewith.

Other routes of action are possible in order to prevent or limit the consequences of aging of the skin, including in particular the stimulation of the synthesis of the structural molecules of the skin, such as collagen, and in particular collagen I, and also filaggrin.

The use according to the invention is a non-therapeutic use and advantageously a cosmetic use; the term "cosmetic" means intended to improve the esthetic appearance of the skin or its appendages such as the nails, especially to retard or reduce physiological modifications in the appearance, arising with age, of individuals in good health. These modifications may appear from the age of 30 or 35, but are generally more pronounced after the age of 40, and become accentuated at 50 and over.

The compounds according to the invention are effective for improving epidermal renewal and for more efficiently combating the signs of aging of the skin.

These compounds therefore find a particular application in cosmetic compositions intended for preventing and/or cosmetically treating aging of the skin; especially preventing and/or treating, in particular topically, the signs of aging of the skin, and most particularly the signs on the skin related to wrinkled skin, skin exhibiting impairment of its viscoelastic or biomechanical properties, skin exhibiting impairment in the cohesion of its tissues, thinned skin and/or skin exhibiting impairment of its surface appearance.

Specifically, it has now been found that 1-phenylmono- or -polyhydroxypropane derivatives are capable of stimulating the activation of AMPK by the keratinocytes.

As explained above, the activation of AMPK, in particular the increase of its phosphorylated form, corresponds to stimulation of the metabolic functions of keratinocytes: these cells are then in a state similar to those of young keratinocytes, and will contribute toward regulating the physiological mechanisms of cutaneous homeostasis.

The use of the compounds according to the invention may make it possible more particularly to maintain and/or restore the biomechanical properties of the skin.

The term "biomechanical properties of the skin" means herein the stretchability, tonicity, firmness, suppleness and/or elasticity properties of the skin.

The term "signs of aging of the skin" means herein any modification of the outer appearance of the skin due to aging, whether it is chronobiological and/or extrinsic aging, in particular photoinduced or hormonal aging; among these signs, it is possible to distinguish:

wrinkled skin, which is reflected especially by the appearance of wrinkles and/or fine lines;

skin exhibiting impairment of its viscoelastic or biomechanical properties, or skin exhibiting a lack of elasticity and/or of stretchability and/or of firmness and/or of suppleness and/or of tonicity, which is reflected in particular by wizened, flaccid, slack or saggy skin;
skin exhibiting impairment of the cohesion of its tissues; thinned skin; and
skin exhibiting impairment of its surface appearance, which is especially reflected by impairment of the grain of the skin, for example roughness.

The invention relates to the non-therapeutic use of a compound of formula (I) as an agent for preventing and/or reducing the signs of aging of the skin, especially the signs on the skin chosen from wrinkled skin, skin exhibiting impairment of its viscoelastic or biomechanical properties, skin exhibiting impairment in the cohesion of its tissues, thinned skin, and skin exhibiting impairment of its surface appearance.

Particularly the invention relates to the use, preferably non-therapeutic, of a compound of formula (I)

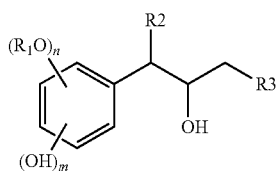

in which
n=0; 1; 2 or 3
m=0; 1; 2 or 3
with $1 \leq m+n \leq 3$
R1 independently denotes a linear C1-C6 alkyl radical or a branched C3-C6 alkyl radical or a linear C1-C6 acyl radical,
R2 and R3 independently denote a hydrogen atom or an OH radical,
and also an optical isomer, stereoisomer and/or diastereoisomer thereof and/or salts thereof, provided that when R1 denotes methyl, R2 denotes a OH radical, and R3 denotes an hydrogen atom then $2 \leq m+n \leq 3$,
as an agent for preventing and/or reducing the signs of aging of the skin, especially the signs on the skin chosen from wrinkled skin, skin exhibiting impairment of its viscoelastic or biomechanical properties, skin exhibiting impairment in the cohesion of its tissues, thinned skin, and skin exhibiting impairment of its surface appearance The invention also relates to a composition, especially a cosmetic composition, comprising, in a physiologically acceptable medium, at least one compound of formula (I) according to the invention.
Particularly the invention relates to a composition, especially a cosmetic composition, comprising, in a physiologically acceptable medium, at least one compound of formula (I) according to the invention, with the exception of the following compound;

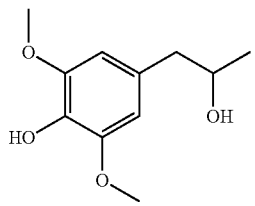

The invention also relates to the non-therapeutic use of a composition, especially a cosmetic composition, comprising, in a physiologically acceptable medium, at least one compound of formula (I).

Particularly the invention relates to the non-therapeutic use of a composition, especially a cosmetic composition, comprising, in a physiologically acceptable medium, at least one compound of formula (I) in which when R1 denotes methyl, R2 denotes a OH radical, and R3 denotes an hydrogen atom then $2 \leq m+n \leq 3$.

The invention also relates to a non-therapeutic cosmetic process for treating the skin, comprising the application to the skin of at least one compound of formula (I) and/or of a cosmetic composition containing at least one compound of formula (I) according to the invention. This process finds an advantageous application in the treatment of the skin, especially of mature skin (skin of individuals with age at least 40) and/or wrinkled skin, in particular of the face, especially of the forehead, the neck, the neckline and/or the hands. A subject of the invention is also a cosmetic treatment process, characterized in that it is intended for promoting the renewal of the keratinocytes and for reducing or preventing signs chosen from thinning of the epidermis, surface wrinkles and impairment of the barrier function.

Particularly the invention relates to a non-therapeutic cosmetic process for treating the skin, comprising the application to the skin of at least one compound of formula (I) in which when R1 denotes methyl, R2 denotes a OH radical, and R3 denotes an hydrogen atom then $2 \leq +n \leq 3$.

Particularly the invention relates a cosmetic composition containing at least one compound of formula (I) according to the invention with the exception of the following compound;

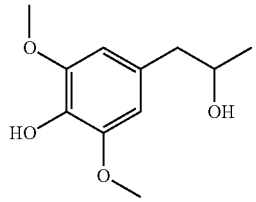

A subject of the present invention is also novel 1-phenyl-mono- or -polyhydroxypropane compounds of formulae (V) to (IX) as defined below.

A subject of the present invention is also compositions, especially cosmetic compositions, comprising, in a physiologically acceptable medium, at least one compound of formulae (V) to (IX).

The invention also relates to the non-therapeutic use of the novel compounds of formulae (V) to (IX) or of a composition, especially a cosmetic composition, of a novel compound of formulae (V) to (IX), in particular as an agent for preventing and/or reducing the signs of aging of the skin, especially the signs on the skin chosen from wrinkled skin, skin exhibiting impairment of its viscoelastic or biomechanical properties, skin exhibiting impairment in the cohesion of its tissues, thinned skin, and skin exhibiting impairment of its surface appearance.

The invention finally relates to a non-therapeutic cosmetic process for treating the skin, comprising the application to the skin of at least one novel compound of formulae (V) to (IX) and/or of a cosmetic composition containing at least one novel compound of formulae (V) to (IX) according to the invention. This process finds an advantageous application in the treatment of the skin, especially of mature skin and/or wrinkled skin, in particular of the face, especially of the forehead, the neck and/or the hands.

The compounds according to the invention thus correspond to formula (I) below:

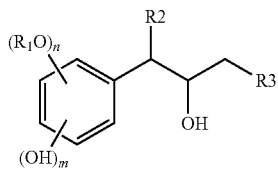

in which
n=0; 1; 2 or 3
m=0; 1; 2 or 3
with 1≤m+n≤3
R1 independently denotes a linear C1-C6 alkyl radical or a branched C3-C6 alkyl radical or a linear C1-C6 acyl radical,
R2 and R3 independently denote a hydrogen atom or a hydroxyl radical,
and also an optical isomer, stereoisomer and/or diastereoisomer thereof and/or salts thereof.

In an embodiment of the invention, the compounds correspond to formula (I) below:

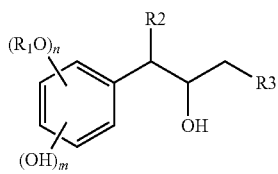

in which
n=0; 1; 2 or 3
m=0; 1; 2 or 3
with 1≤m+n≤3
R1 independently denotes a linear C1-C6 alkyl radical or a branched C3-C6 alkyl radical or a linear C1-C6 acyl radical,
R2 and R3 independently denote a hydrogen atom or an OH radical,
and also an optical isomer, stereoisomer and/or diastereoisomer thereof and/or salts thereof, provided that when R1 denotes methyl, R2 denotes a OH radical, and R3 denotes a hydrogen atom then 2≤m+n≤3.

Salts of compounds of formula (I) may be organic salts and/or minerals. They may be chosen from metal salts, for example aluminum (Al3+), zinc (Zn2+), manganese (Mn2+) or copper (Cu2+); alkali metal salts, for example lithium (Li+), sodium (Na+) or potassium (K+); and alkaline earth metal salts, for example calcium (Ca2+) or magnesium (Mg2+). It may also include salts of formula NH4+ or organic salts of formula NHX3+, NX3 designating an organic amine, the radicals X being identical or different, two or three X radicals can form in pairs a ring with the nitrogen atom which carries them or NX3 possibly denotes an aromatic amine. Organic amines denote in particular alkylamines, such as methylamine, dimethylamine, trimethylamine, triethylamine or ethylamine; hydroxyalkylamines such as 2-hydroxyethylamine, bis-(2-hydroxyethyl) amine or tri-(2-hydroxyethyl) amine; cycloalkylamines such as bicyclohexylamine or glucamine, piperidine; pyridines and the like, for example collidine, quinine or quinoline; and amino acids with basic character, as for example the lysine or arginine.

Preferably salts compounds of formula (I) are calcium salts.
Preferably:
n=0; 1; 2 or 3
m=0; 1; 2 or 3
with 2≤m+n≤3
R1 independently denotes a linear C1-C6 alkyl radical or a branched C3-C6 alkyl radical or a linear C1-C6 acyl radical,
R2 and R3 independently denote a hydrogen atom or an OH radical.
Preferably:
n=0; 1; 2 or 3
m=0; 1; 2 or 3
with 1≤m+n≤3
Each of the substituents R1 independently denotes a linear C1-C4 alkyl radical
R2 and R3 independently denote a hydrogen atom or a hydroxyl radical,
and also an optical isomer, stereoisomer and/or diastereoisomer thereof.

Preferentially, the linear saturated or branched alkyl groups may be chosen from methyl, ethyl, propyl, isopropyl, butyl, isobutyl and tert-butyl, more preferentially methyl.
Preferably:
n=0; 1; 2 or 3
m=0; 1; 2 or 3
with 2≤m+n≤3
each of the substituents R1 independently denotes a linear C1-C4 alkyl radical; preferably denotes methyl;
R2 and R3 independently denote a hydrogen atom or a hydroxyl radical.
Even more preferably,
n=0; 1; 2 or 3
m=0; 1; 2 or 3
with 2≤m+n≤3
Each of the substituents R1 denotes methyl
R2 and R3 independently denote a hydrogen atom or a hydroxyl radical,
and also an optical isomer, stereoisomer and/or diastereoisomer thereof.

In a first preferred variant of the invention, among the compounds of formula (I), or an optical isomer, stereoisomer and/or diastereoisomer thereof and/or salts thereof, the compounds for which R2 denotes a hydrogen atom or a hydroxyl radical and R3 denotes a hydrogen atom will preferably be chosen,
i.e. the compounds corresponding to formula (II) below:

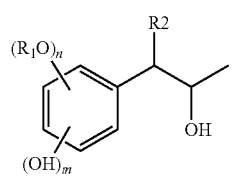

in which:
n=0; 1; 2 or 3
m=0; 1; 2 or 3 with 1≤m+n≤3
each of the substituents R1 independently denotes a linear C1-C6 alkyl radical or a branched C3-C6 alkyl radical or a linear C1-C6 acyl radical,
R2 denotes a hydrogen atom or a hydroxyl radical.
Preferably:
n=0; 1; 2 or 3
m=0; 1; 2 or 3
with 2≤m+n≤3
R1 independently denotes a linear C1-C6 alkyl radical or a branched C3-C6 alkyl radical or a linear C1-C6 acyl radical,
R2 and R3 independently denote a hydrogen atom or an OH radical.
Preferably:
n=0; 1; 2 or 3
m=0; 1; 2 or 3
with 1≤m+n≤3
each of the substituents R1 independently denotes a linear C1-C4 alkyl radical
R2 denotes a hydrogen atom or a hydroxyl radical.
Preferably:
n=0, 1, 2 or 3
m=0; 1; 2 or 3
with 2≤m+n≤3
each of the substituents R1 independently denotes a linear C1-C4 alkyl radical; preferably denotes methyl;
R2 and R3 independently denote a hydrogen atom or a hydroxyl radical.
Even more preferably,
n=0; 1; 2 or 3
m=0; 1; 2 or 3
with 2≤m+n≤3
R1 denotes methyl
R2 denotes a hydrogen atom or a hydroxyl radical.
Among the compounds of formula (II), compounds 1 to 4 and 7 below, the optical isomers, stereoisomers and diastereoisomers thereof and/or geometrical isomers thereof and/or salts thereof will be chosen more particularly:

| Compound | Structure |
|---|---|
| 1 | 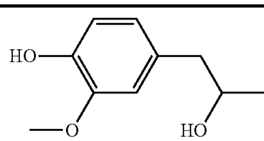 |
| 2 | 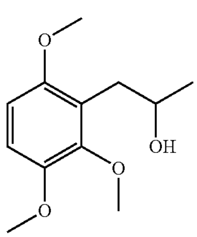 [SMILES: COc1ccc(OC)c(OC)c1CC(C)O] |
| 3 | 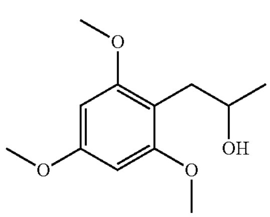 [SMILES: COc1cc(OC)c(CC(C)O)c(OC)c1] |
| 4 | |
| | |

In a second preferred variant of the invention, among the compounds of formula (I), or an optical isomer, stereoisomer and/or diastereoisomer thereof and/or salts thereof, the compounds for which R2 denotes a hydrogen atom and R3 denotes a hydroxyl radical, i.e. the compounds corresponding to formula (III), will preferably be chosen,

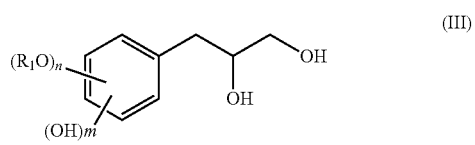

(III)

in which:
n=0; 1; 2 or 3
m=0; 1; 2 or 3
with 1≤m+n≤3
each of the substituents R1 independently denotes a linear C1-C6 alkyl radical or a branched C3-C6 alkyl radical or a linear C1-C6 acyl radical,
Preferably:
n=0; 1; 2 or 3
m=0; 1; 2 or 3
with 1≤m+n≤3
each of the substituents R1 independently denotes a linear C1-C4 alkyl radical.
Even more preferably,
n=0; 1; 2 or 3
m=0; 1; 2 or 3
with 2≤m+n≤3
R1 denotes methyl
Among the compounds of formula (III), compounds 5 and 6 below, the optical isomers, stereoisomers and diastereoisomers thereof or geometrical isomers thereof and/or salts thereof will be chosen more particularly preferably, and even more particularly compound 5:

| Compound | Structure |
|---|---|
| 5 | 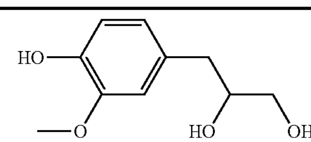 |

| Compound | Structure |
|---|---|
| 6 | 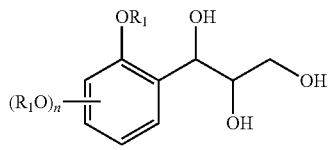 |

Preferably among the compounds of formula (III), calcium salts of compounds 5 and 6 above will be chosen more particularly, and even more particularly calcium salt of compound 5.

A subject of the invention is also the novel compounds of formulae (V) to (IX) below:

Formula (V):

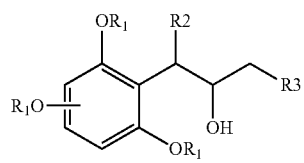 (V)

in which:
n=1 or 2
each of the substituents R1 independently denotes a hydrogen atom or a linear C1-C6 alkyl or a branched C3-C6 alkyl Formula (VI):

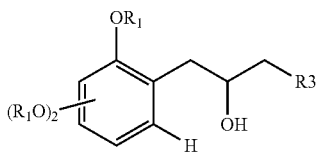 (VI)

in which:
when R2 denotes a hydroxyl radical, then R3 denotes a hydrogen atom,
when R2 denotes a hydrogen atom, then R3 denotes a hydroxyl radical,
each of the substituents R1 independently denotes a hydrogen atom or a linear C1-C6 alkyl or a branched C3-C6 alkyl Formula (VII):

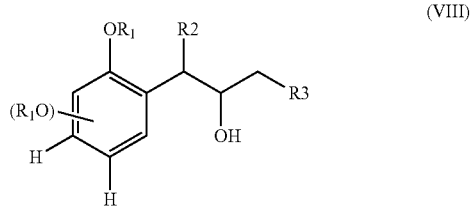 (VII)

in which:
R3 denotes a hydrogen atom or a hydroxyl radical
each of the substituents R1 independently denotes a hydrogen atom or a linear C1-C6 alkyl or a branched C3-C6 alkyl Formula (VIII):

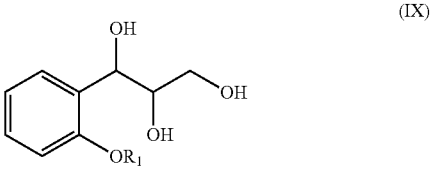 (VIII)

in which:
when R2 denotes a hydroxyl radical, then R3 denotes a hydrogen atom,
when R2 denotes a hydrogen atom, then R3 denotes a hydroxyl radical,
each of the substituents R1 independently denotes a hydrogen atom or a linear C1-C6 alkyl or a branched C3-C6 alkyl Formula (IX):

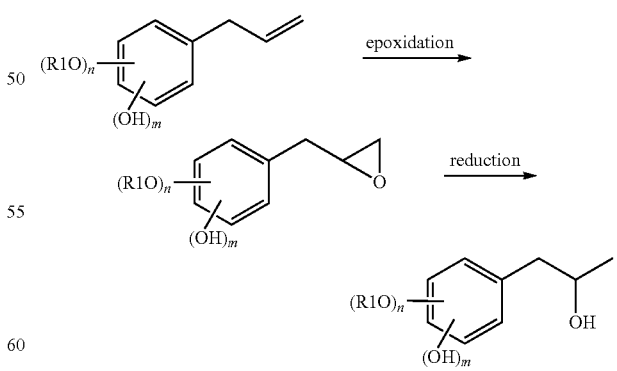 (IX)

in which R1 denotes a hydrogen or a linear C1-C6 alkyl or a branched C3-C6 alkyl.

The compounds corresponding to formula (I) may be prepared according to four reaction sequences, depending on the substitution unit of the propane unit (values of R2 and R3).

Case where R2=R3=H m, n and R1 having the same meaning as previously.

A solution of m-CPBA (1-5 eq.) in an aprotic solvent such as dichloromethane is added dropwise to the alkene predissolved in the same solvent. The reaction mixture is stirred (0° C.-50° C.) for 1-72 hours and then worked up with aqueous Na$_2$SO$_3$ solution (conc. 5-20%) to neutralize the excess oxidizing agent. The phases are separated and the organic phase is washed twice with a basic aqueous solution such as aqueous 10% NaHCO$_3$ solution, dried and concentrated. The residue may be purified by column chromatography on silica gel.

Advantageously, when m=0, compound (I) may be obtained directly by alkylation of the corresponding phenol derivative.

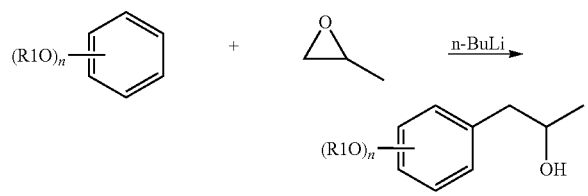

R1 and n having the same meaning as previously.

Propylene oxide (1-10 eq.) is added dropwise to a solution of the phenol derivative (1 eq.) in an organic solvent such as THF at 0-70° C. A solution of n-BuLi in hexane (for example a commercial 1.6 M solution (0.1-2 eq.) is added dropwise and the reaction mixture is then stirred at room temperature for 1-24 hours. The excess base is neutralized by adding saturated aqueous NH$_4$Cl solution and the mixture is extracted with an organic solvent such as ethyl acetate or dichloromethane. The organic phases are combined, dried and concentrated. The residue is purified by column chromatography on silica gel.

Case where R2=OH, R3=H

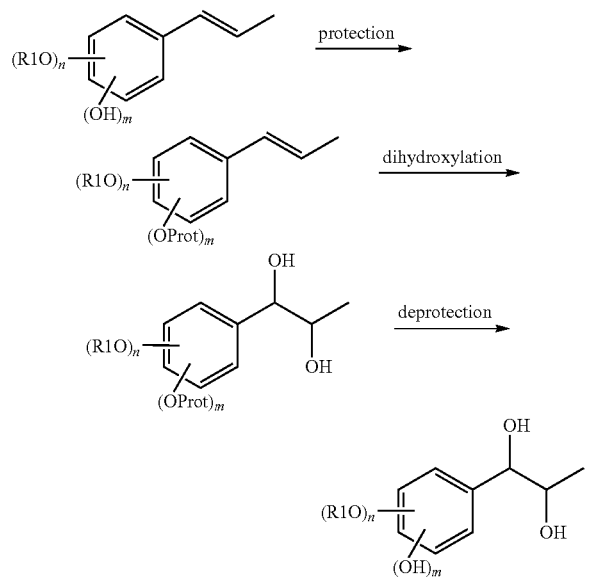

R1, m and n having the same meaning as previously.

When m≥1, Prot denotes a hydroxyl-function protecting group, in particular —CO—CH$_3$ or CH$_2$-Ph.

a) protection of the free phenol functions according to the standard methods known to those skilled in the art (see, for example, *Greene's Protective Groups in Organic Synthesis*, P. G. M. Wutz, T. Greene, ed. Wiley-Blackwell), for example by using the acetate group or the benzyl group as protecting group;

b) dihydroxylation of the corresponding protected styrenes: The reaction may be performed using the commercial Sharpless systems AD-mix-α (available from the supplier Sigma USA under the reference 392758) or AD-mix-β (available from the supplier Sigma USA under the reference 392766). The oxidizing system AD-mix (1-3 eq.) and the protected styrene derived from the first step are dissolved in an alkanol water two-phase mixture such as the t-BuOH/water mixture in 1/1 proportions and the medium is stirred at 0-50° C. until dissolution is complete.

The reaction medium is heated at 0-70° C. for 2-96 hours. After cooling to room temperature, it is stirred in contact with sodium sulfite to neutralize the peroxides. The product is extracted with an organic solvent such as ethyl acetate and the organic phases are combined, dried and concentrated. The residue is purified by column chromatography on silica gel.

c) deprotection of the phenol functions, protected beforehand, according to the standard methods known to those skilled in the art (see, for example, *Greene's Protective Groups in Organic Synthesis*, P. G. M. Wutz, T. Greene, ed. Wiley-Blackwell)

Case where R2=OH, R3=OH

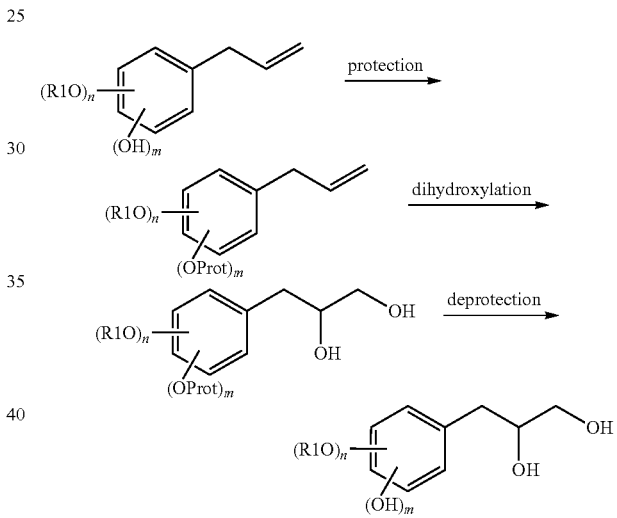

R1, m and n having the same meaning as previously.

When m≥1, Prot denotes a hydroxyl-function protecting group, in particular —CO—CH$_3$ or CH$_2$-Ph.

a) protection of the free phenol functions according to the standard methods known to those skilled in the art (see, for example, *Greene's Protective Groups in Organic Synthesis*, P. G. M. Wutz, T. Greene, ed. Wiley-Blackwell), for example by using the acetate group or the benzyl group as protecting group;

b) dihydroxylation of the corresponding protected alkenes: The reaction may be performed using the commercial Sharpless systems AD-mix-α (available from the supplier Sigma USA under the reference 392758) or AD-mix-β (available from the supplier Sigma USA under the reference 392766). The oxidizing system AD-mix (1-3 eq.) and the protected alkene derived from the first step are dissolved in an alkanol water two-phase mixture such as the t-BuOH/water mixture in 1/1 proportions and the medium is stirred at 0-50° C. until dissolution is complete.

The reaction medium is heated at 0-70° C. for 2-96 hours. After cooling to room temperature, it is stirred in contact with sodium sulfite to neutralize the peroxides. The product is extracted with an organic solvent such as ethyl acetate and the organic phases are combined, dried and concentrated. The residue is purified by column chromatography on silica gel.

Alternatively, this dihydroxylation may be performed via an epoxidation/hydrolysis sequence. A solution of m-CPBA (1-5 eq.) in an aprotic solvent such as dichloromethane is added dropwise to the protected alkene derived from the first step (1 eq.), predissolved in the same solvent. The reaction mixture is stirred (0° C.-50° C.) for 1-72 hours and then worked up with aqueous $Na_2SO_3$ solution (conc. 5-20%) to neutralize the excess oxidizing agent. The phases are separated and the organic phase is washed twice with a basic aqueous solution such as aqueous 10% $NaHCO_3$ solution, dried and concentrated. The residue is purified by column chromatography on silica gel.

The product thus isolated is dissolved in an aprotic solvent such as dichloromethane and an acidic aqueous solution, such as aqueous 1-20% sulfuric acid solution, is added at 0-30° C. The reaction mixture is stirred at room temperature for 1-96 hours and the solvent is then removed by evaporation. The aqueous solution obtained is extracted three times with an organic solvent, such as ethyl acetate or diethyl ether. The organic phases are combined, dried and then concentrated under reduced pressure. The residue is purified by column chromatography on silica gel.

c) deprotection of the phenol functions, protected beforehand, according to the standard methods known to those skilled in the art (see, for example, *Greene's Protective Groups in Organic Synthesis*, P. G. M. Wutz, T. Greene, ed. Wiley-Blackwell)

Case where R2=R3=OH

The derivatives of formula (I) such that R2=R3=OH may be obtained by dihydroxylation of the corresponding allylic alcohols, protected beforehand.

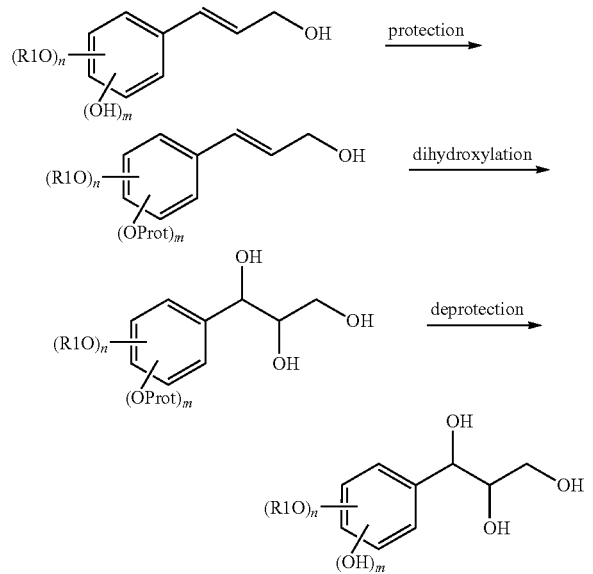

R1, m and n having the same meaning as previously.
When m≥1, Prot denotes a hydroxyl-function protecting group, in particular —CO—$CH_3$ or $CH_2$-Ph.

a) protection of the free phenol functions according to the standard methods known to those skilled in the art (see, for example, *Greene's Protective Groups in Organic Synthesis*, P. G. M. Wutz, T. Greene, ed. Wiley-Blackwell), for example by using the acetate group or the benzyl group as protecting group;

b) dihydroxylation of the protected allylic alcohols:
The reaction may be performed using the commercial Sharpless systems AD-mix-α (available from the supplier Sigma USA under the reference 392758) or AD-mix-β (available from the supplier Sigma USA under the reference 392766). The oxidizing system AD-mix (1-3 eq.) and the protected alkene derived from the first step are dissolved in an alkanol water two-phase mixture such as the t-BuOH/water mixture in 1/1 proportions and the medium is stirred at 0-50° C. until dissolution is complete.

The reaction medium is heated at 0-70° C. for 2-96 hours. After cooling to room temperature, it is stirred in contact with sodium sulfite to neutralize the peroxides. The product is extracted with an organic solvent such as ethyl acetate and the organic phases are combined, dried and concentrated. The residue is purified by column chromatography on silica gel.

c) deprotection of the phenol functions, protected beforehand, according to the standard methods known to those skilled in the art (see, for example, *Greene's Protective Groups in Organic Synthesis*, P. G. M. Wutz, T. Greene, ed. Wiley-Blackwell)

According to these routes, the compounds of formulae (I), (II), (III) and in particular the novel compounds of formulae (V) to (IX) are obtained.

The present invention also relates to a composition, especially a cosmetic composition, comprising, in a physiologically acceptable medium, at least one compound of formula (I) and preferably at least one compound chosen from compounds 1 to 7 described previously.

In a particular embodiment, the invention relates to a composition, especially a cosmetic composition, comprising, in a physiologically acceptable medium, at least one compound of formula (I) as defined above, provided that the composition do not comprises hydrogen peroxide.

Particularly the invention relates to a composition, especially a cosmetic composition, comprising, in a physiologically acceptable medium, at least one compound of formula (I) as defined above, with the exception of the following compound;

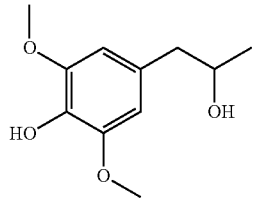

In particular, the composition is suitable for topical application to the skin.

The present invention also relates to a composition, especially a cosmetic composition, comprising, in a physiologically acceptable medium, at least one novel compound of formulae (V) to (IX).

The compound of formulae (I) and (V) to (IX) may be present, alone or as a mixture, in the compositions according to the invention in an amount of between 0.01% and 30% by weight, preferably between 0.1 and 10% by weight, especially between 0.5% and 5% by weight, relative to the total weight of the composition.

The compositions according to the invention also comprise a physiologically acceptable medium, which will preferentially be a cosmetically acceptable medium, i.e. a medium that has no unpleasant odor, color or appearance, and that does not cause the user any unacceptable stinging, tautness or redness. For the purposes of the present invention, the term "physiologically acceptable medium" means a medium that is compatible with human keratin materials such as the skin of the body or of the face, the lips, mucous membranes, the eyelashes or the nails.

The compositions according to the invention may comprise any cosmetic ingredient usually used in the field of application envisioned.

Thus, a composition according to the invention may comprise at least one cosmetic ingredient chosen from water; organic solvents, in particular C1-C6 alcohols and C2-C10 carboxylic acid esters; hydrocarbon-based oils, silicone oils, fluoro oils, waxes, pigments, fillers, dyes, surfactants, emulsifiers, cosmetic active agents, UV-screening agents, film-forming polymers, hydrophilic or lipophilic gelling agents, hydrophilic or lipophilic thickeners, preserving agents, fragrances, odor absorbers/neutralizers and antioxidants.

These optional ingredients may be present in the composition in a proportion of from 0.001% to 99% by weight and especially from 0.01% to 40% by weight relative to the total weight of the composition.

The compositions according to the invention may be compositions that may comprise a fatty phase and/or an aqueous phase.

Depending on their nature, these optional ingredients may be introduced into the fatty phase or into the aqueous phase of the composition, or into lipid vesicles. In any case, these ingredients, and the proportions thereof, will be chosen by a person skilled in the art such that the advantageous properties of the compounds according to the invention are not, or are not substantially, adversely affected by the envisaged addition.

As oils that may be used in the invention, mention may be made of mineral oils, hydrocarbon-based oils such as liquid petroleum jelly, oils of plant origin, oils of animal origin, synthetic oils and silicone-based oils. When it is present, the fatty phase may also contain fatty alcohols, fatty acids or waxes.

As hydrophilic thickeners or gelling agents, mention may be made of carboxyvinyl polymers (carbomer), acrylic copolymers such as acrylate/alkyl acrylate copolymers, polyacrylamides, polysaccharides, natural gums and clays, and, as lipophilic thickeners or gelling agents, mention may be made of modified clays such as bentones, metal salts of fatty acids and hydrophobic silica.

A composition according to the invention may comprise at least one cosmetic active agent other than the compounds of formula (I), in particular at least one compound chosen from: desquamating agents; moisturizers; depigmenting or propigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; dermo-decontracting agents; tensioning agents; agents acting on microcirculation; agents acting on the energy metabolism of cells; and mixtures thereof.

This composition may be in any galenical form normally used in the cosmetic or dermatological field, and especially in the form of an optionally gelled aqueous or aqueous-alcoholic solution, a dispersion, optionally a two-phase dispersion, of the lotion type, an emulsion obtained by dispersion of a fatty phase in an aqueous phase (O/W) or vice versa (W/O), or a triple (W/O/W or O/W/O) emulsion or a vesicular dispersion of ionic and/or nonionic type; aqueous or oily gels. These compositions are prepared according to the usual methods.

The composition may be more or less fluid and may have the appearance of a white or colored cream, an ointment, a milk, a lotion, a serum, a paste, a gel or a mousse. It may optionally be applied in the form of an aerosol. It may also be in solid form, in particular in stick form.

When the composition is an emulsion, the proportion of the fatty phase can range from 5% to 80% by weight and preferably from 8% to 50% by weight, with respect to the total weight of the composition. The emulsifiers may be present in a proportion ranging from 0.3% to 30% by weight and preferably from 0.5% to 20% by weight, relative to the total weight of the composition.

The composition according to the invention may constitute a skincare composition, in particular a cleansing, protection, treatment, or care cream for the face, for the hands, for the feet, for the major anatomical folds or for the body (for example, day creams, night creams, makeup-removing creams, foundation creams, antisun creams); a makeup-removing milk, a protective or care body milk or, an antisun milk; or a lotion, a gel or foam for skincare, such as a cleansing lotion.

A composition according to the invention is advantageously an anti-aging composition, especially a care composition for treating and/or combating, especially cosmetically, the external signs of aging of the skin.

The composition is more particularly a composition for caring for mature skin.

The composition may also be a makeup composition, especially a foundation.

In the description and in the examples that follow, unless otherwise mentioned, the percentages are weight percentages and the ranges of values written in the form "between . . . and . . . " include the stated lower and upper limits. The ingredients are mixed, before being formed, in the order and under conditions that are easily determined by those skilled in the art.

The examples hereinafter are presented as nonlimiting illustrations of the field of the invention.

EXAMPLE 1—SYNTHESIS OF COMPOUND 1

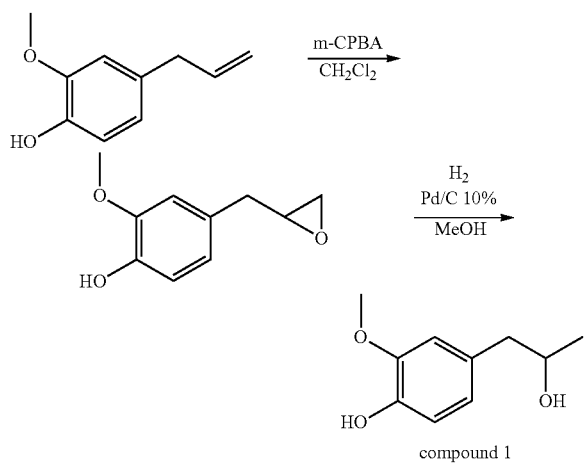

compound 1

1st Step

A solution of m-CPBA (22.3 g, 129.3 mmol, 2 eq.) in dichloromethane is added dropwise to eugenol (10.6 g, 64.6 mmol, 1 eq.) predissolved in dichloromethane (100 mL). The reaction mixture is stirred at room temperature for 12 hours and then worked up with aqueous $Na_2SO_3$ solution (conc. 10%, 200 mL) to neutralize the oxidizing agent. The phases are separated and the organic phase is washed twice with aqueous 10% $NaHCO_3$ solution, dried over $Na_2SO_4$ and concentrated. The residue is purified by column chromatography on silica gel (hexane/EtOAc: 25/1) to give the epoxide intermediate (6.4 g, 55% yield).

2nd Step

A solution of the intermediate epoxide (6.4 g, 35.5 mmol), obtained from the first step, in methanol (80 mL) is stirred in the presence of 10% Pd/C catalyst (1.0 g) under an atmosphere of dihydrogen for 24 hours. The catalyst is removed by filtration and the filtrate is then concentrated to dryness. The residue is purified by column chromatography on silica gel (hexane/EtOAc: 5/1) to give compound 1 in the form of a white powder (2.9 g, 45% yield).

The $^1$H NMR spectra and mass spectra are in accordance with the expected structure.

EXAMPLE 2—SYNTHESIS OF COMPOUND 2

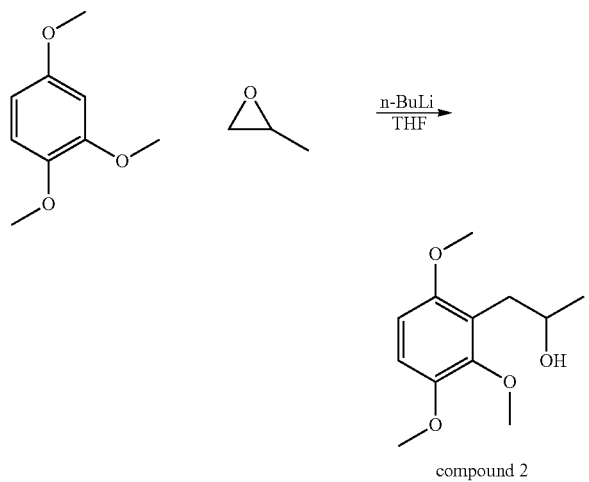

compound 2

Propylene oxide (8.3 g, 142.8 mmol) is added dropwise to a solution of 1,3,4-trimethoxybenzene (6.0 g, 35.7 mmol) in THF (100 mL) at 40° C. The reaction mixture is maintained at this temperature for 2 hours and then cooled to room temperature. A solution of n-BuLi in hexane (1.6 M, 17.1 mL, 14.4 mmol) is added dropwise and the reaction mixture is then stirred at room temperature for 1 hour. The excess base is neutralized by adding saturated aqueous $NH_4Cl$ solution (20 mL) and the mixture is extracted 3 times with 50 mL of ethyl acetate. The organic phases are combined, dried over $Na_2SO_4$ and concentrated. The residue is purified by column chromatography on silica gel (hexane/EtOAc: 10/1) to isolate compound 2 in the form of a pale yellow oil (4.2 g, 52% yield).

The $^1$H NMR spectra and mass spectra are in accordance with the expected structure.

EXAMPLE 3—SYNTHESIS OF COMPOUND 3

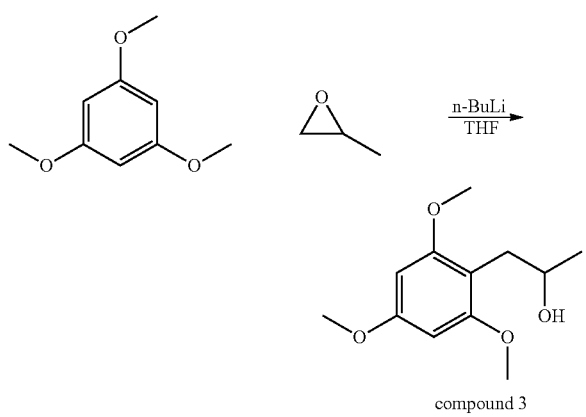

compound 3

Propylene oxide (2.8 g, 48 mmol) is added dropwise to a solution of 1,2,5-trimethoxybenzene in THF (100 mL) at 40° C. The reaction mixture is maintained at this temperature for 2 hours and then cooled to room temperature. A solution of n-BuLi in hexane (1.6 M, 9 mL, 14.4 mmol) is added dropwise and the reaction mixture is then stirred at room temperature for 1 hour. The excess base is neutralized by adding saturated aqueous $NH_4Cl$ solution (20 mL) and the mixture is extracted 3 times with 50 mL of ethyl acetate. The organic phases are combined, dried over $Na_2SO_4$ and concentrated. The residue is purified by column chromatography on silica gel (hexane/EtOAc: 10/1) to isolate compound 3 in the form of a white powder (500 mg, 18% yield).

The $^1$H NMR spectra and mass spectra are in accordance with the expected structure.

EXAMPLE 4—SYNTHESIS OF COMPOUND 4

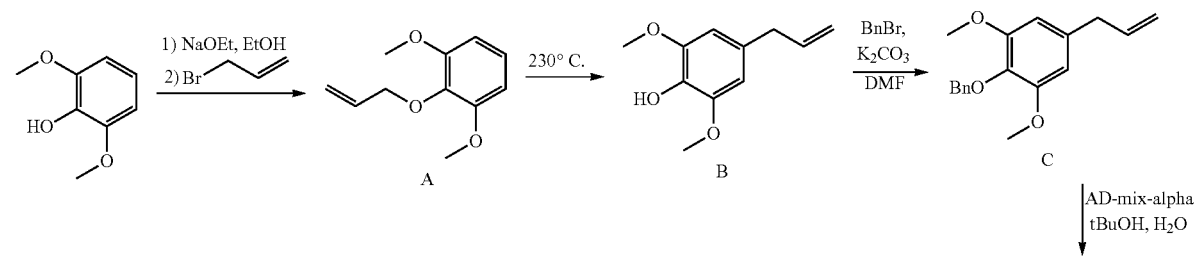

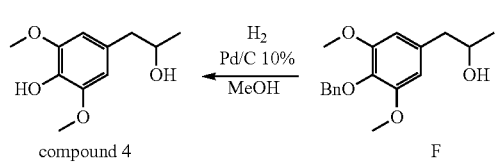 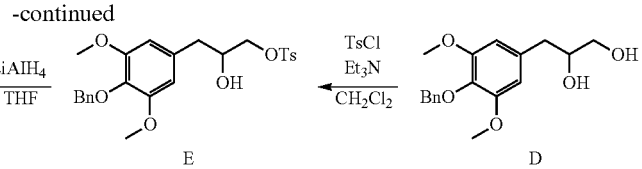

1st Step

The sodium ethoxide solution is prepared by adding sodium (4.0 g, 174 mmol) portionwise to absolute ethanol (500 mL) at 0° C. After total consumption of the sodium, 2,6-dimethoxyphenol (19.8 g, 129 mmol) is added dropwise at 0° C. under an inert atmosphere. After addition, the reaction medium is stirred at room temperature for 2 hours. 3-Bromopropene (20 g, 165 mmol) is then added dropwise and the medium is stirred for 16 hours. After concentrating under reduced pressure, the residue is dissolved in water and extracted with dichloromethane. The organic phases are combined, dried over $Na_2SO_4$ and concentrated. The residue is purified by column chromatography on silica gel (hexane/EtOAc: 5/1) to give intermediate A in the form of a brown oil (20.0 g, 81% yield).

2nd Step

Intermediate A is heated with stirring at 230° C. for 2 hours. The crude product thus obtained is purified by column chromatography on silica gel (hexane/EtOAc: 5/1) to give intermediate B in the form of a colorless oil (16.0 g, 80% yield).

3rd Step

A mixture consisting of intermediate B (1.94 g, 10 mmol, 1 eq.), benzyl bromide (2.05 g, 12 mmol, 1.2 eq.) and potassium carbonate (2.07 g, 15 mmol, 1.5 eq.) in N,N-dimethylformamide (30 mL) is stirred at room temperature for 16 hours. The reaction medium is diluted by adding ethyl acetate and washed with saturated aqueous sodium chloride solution. The organic phase is dried over $Na_2SO_4$ and concentrated. The residue is purified by column chromatography on silica gel (hexane/EtOAc: 5/1) to give intermediate C in the form of a yellowish oil (2.0 g, 70% yield).

4th Step

Intermediate C (1.0 g, 3.5 mmol, 1 eq.) and the oxidizing system AD-mix-α (5 g, 3.5 mmol) in 50 mL of a water/t-BuOH mixture (1/1) are stirred at room temperature for 16 hours. The reaction medium is then diluted in water and extracted with ethyl acetate. The organic phases are combined, washed with aqueous $Na_2SO_3$ solution and then with saturated aqueous NaCl solution, dried over $Na_2SO_4$ and concentrated under vacuum. The residue is purified by column chromatography on silica gel (hexane/EtOAc: 1/1) to give intermediate D in the form of a white solid (1.0 g, 90% yield).

5th Step

Intermediate D (1.0 g, 3.3 mmol, 1 eq.) in dichloromethane (25 mL) is treated at 0° C. with tosyl chloride (760 mg, 4.0 mmol, 1.2 eq.) in the presence of triethylamine (710 mg, 7.0 mmol, 2.1 eq.). The reaction medium is stirred at 0° C. for 3 hours and then at room temperature for 16 hours. The mixture is then washed with aqueous $H_2SO_4$ solution (5%), then with aqueous $NaHCO_3$ solution (5%) and then with saturated aqueous NaCl solution. The organic phase is then dried over $Na_2SO_4$ and concentrated. The residue is purified by column chromatography on silica gel (hexane/EtOAc: 3/1) to give intermediate E in the form of a white solid (900 mg, 60% yield).

6th Step

Intermediate E (900 mg, 1.9 mmol, 1 eq.) predissolved in THF (5 mL) is added dropwise to a suspension of $LiAlH_4$ (100 mg, 2.6 mmol) in THF (5 mL) at 0° C. The reaction medium is then stirred at room temperature for 5 hours. The mixture is poured onto a mixture of ice-water (10 mL) and aqueous 5N HCl solution (5 mL) and then extracted 3 times with ethyl acetate. The organic phases are combined, washed with saturated aqueous NaCl solution, dried over $Na_2SO_4$ and concentrated. The residue is purified by column chromatography on silica gel (hexane/EtOAc: gradient 3/1 to 1/1) to give intermediate F in the form of a white solid (500 mg, 60% yield).

7th Step

Intermediate F (500 mg, 6.3 mmol) dissolved in ethanol (10 mL) is placed in contact with 10% Pd/C catalyst (10 mg). The reaction mixture is stirred under dihydrogen (0.1 MPa) at room temperature for 16 hours. The catalyst is removed by filtration and the filtrate is then concentrated. The residue is purified by column chromatography on silica gel (hexane/EtOAc: gradient 2/1 to 1/1) to give compound 4 in the form of a white solid (200 mg, 57% yield).

The $^1H$ NMR spectra and mass spectra are in accordance with the expected structure.

EXAMPLE 5—SYNTHESIS OF COMPOUND 5

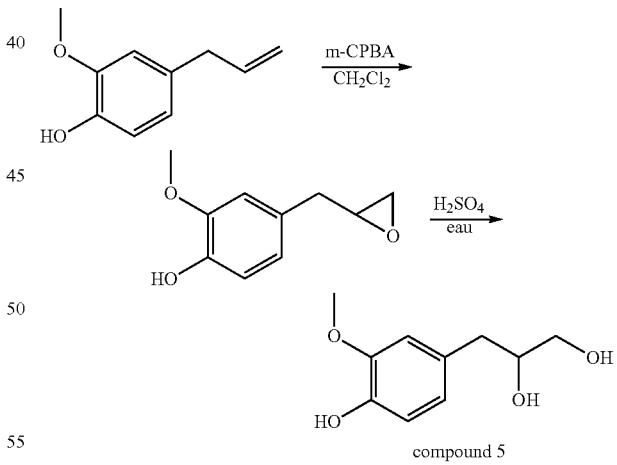

1st Step

A solution of m-CPBA (22.3 g, 129.3 mmol, 2 eq.) in dichloromethane is added dropwise to eugenol (10.6 g, 64.6 mmol, 1 eq.) predissolved in dichloromethane (100 mL). The reaction mixture is stirred at room temperature for 12 hours and then worked up with aqueous $Na_2SO_3$ solution (conc. 10%, 200 mL) to neutralize the oxidizing agent. The phases are separated and the organic phase is washed twice with aqueous 10% $NaHCO_3$ solution, dried over $Na_2SO_4$ and concentrated. The residue is purified by column chromatography on silica gel (hexane/EtOAc: 25/1) to give the epoxide intermediate (6.4 g, 55% yield).

2nd Step

A solution of the intermediate epoxide (6.4 g, 35.5 mmol), obtained from the first step, in dichloromethane (50 mL) is treated with 50 mL of water and then 25 mL of aqueous 5% $H_2SO_4$ solution. The reaction mixture is stirred at room temperature for 24 hours and the dichloromethane is then removed by evaporation. The aqueous solution obtained is extracted three times with ethyl acetate. The organic phases are combined, dried over $Na_2SO_4$ and then concentrated under reduced pressure. The residue is purified by column chromatography on silica gel ($CH_2Cl_2$/MeOH=20/1) to give compound 5 in the form of a yellow/orange oil (4.6 g, 65% yield).

The $^1$H NMR spectra and mass spectra are in accordance with the expected structure.

EXAMPLE 6—SYNTHESIS OF COMPOUND 6

3rd Step

A mixture consisting of intermediate B (1.94 g, 10 mmol, 1 eq.), benzyl bromide (2.05 g, 12 mmol, 1.2 eq.) and potassium carbonate (2.07 g, 15 mmol, 1.5 eq.) in N,N-dimethylformamide (30 mL) is stirred at room temperature for 16 hours. The reaction medium is diluted by adding ethyl acetate and washed with saturated aqueous sodium chloride solution. The organic phase is dried over $Na_2SO_4$ and concentrated. The residue is purified by column chromatography on silica gel (hexane/EtOAc: 5/1) to give intermediate C in the form of a yellowish oil (2.0 g, 70% yield).

4th Step

Intermediate C (1.0 g, 3.5 mmol, 1 eq.) and the oxidizing system AD-mix-α (5 g, 3.5 mmol, 1 eq.) in 50 mL of a water/t-BuOH mixture (1/1) are stirred at room temperature for 16 hours. The reaction medium is then diluted in water and extracted with ethyl acetate. The organic phases are combined, washed with aqueous $Na_2SO_3$ solution and then with saturated aqueous NaCl solution, dried over $Na_2SO_4$

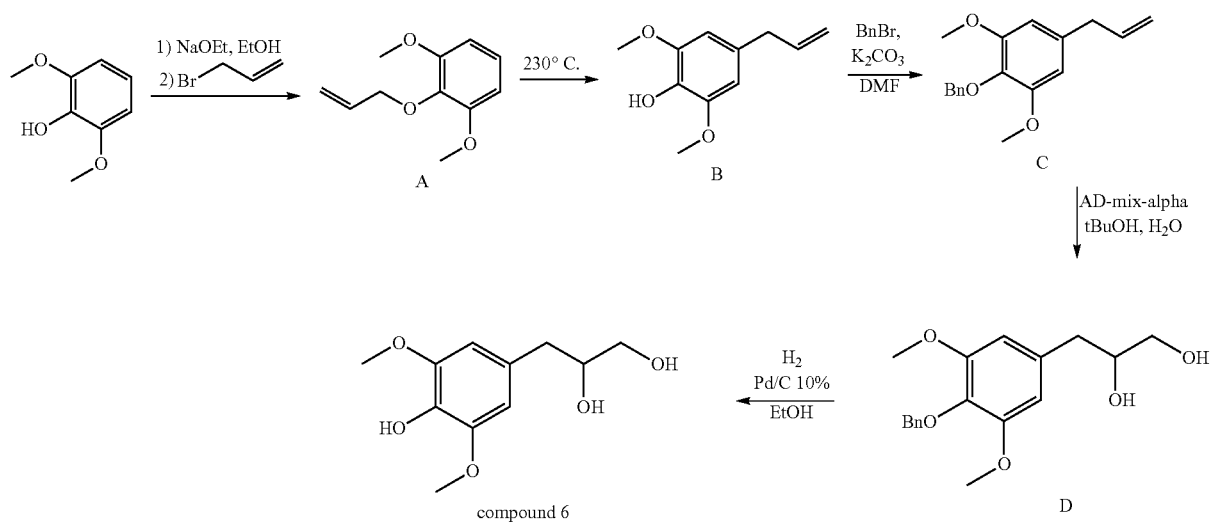

1st Step

The sodium ethoxide solution is prepared by adding sodium (4.0 g, 174 mmol) portionwise to absolute ethanol (500 mL) at 0° C. After total consumption of the sodium, 2,6-dimethoxyphenol (19.8 g, 129 mmol) is added dropwise at 0° C. under an inert atmosphere. After addition, the reaction medium is stirred at room temperature for 2 hours. 3-Bromopropene (20 g, 165 mmol) is then added dropwise and the medium is stirred for 16 hours. After concentrating under reduced pressure, the residue is dissolved in water and extracted with dichloromethane. The organic phases are combined, dried over $Na_2SO_4$ and concentrated. The residue is purified by column chromatography on silica gel (hexane/EtOAc: 5/1) to give intermediate A in the form of a brown oil (20.0 g, 81% yield).

2nd Step

Intermediate A is heated with stirring at 230° C. for 2 hours. The crude product thus obtained is purified by column chromatography on silica gel (hexane/EtOAc: 5/1) to give intermediate B in the form of a colorless oil (16.0 g, 80% yield).

and concentrated. The residue is purified by column chromatography on silica gel (hexane/EtOAc: 1/1) to give intermediate D in the form of a white solid (1.0 g, 90% yield).

5th Step

Intermediate D (2.0 g, 6.3 mmol) dissolved in ethanol (10 mL) is placed in contact with 10% Pd/C catalyst (10 mg). The reaction mixture is stirred under dihydrogen (0.1 MPa) at room temperature for 16 hours. The catalyst is removed by filtration and the filtrate is then concentrated. The residue is purified twice by column chromatography on silica gel (hexane/EtOAc: gradient 1/2). To obtain a higher purity, the product is then recrystallized from an EtOH/hexane mixture and compound 6 is isolated in the form of a white solid (1.3 g, 90% yield).

The $^1$H NMR spectra and mass spectra are in accordance with the expected structure.

EXAMPLE 7—SYNTHESIS OF COMPOUND 7

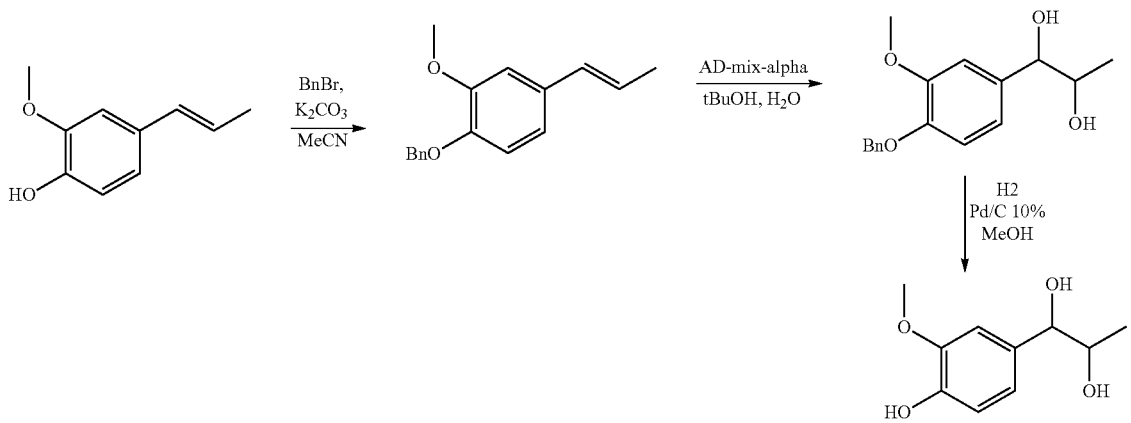

1st Step: Protection of Isoeugenol

A mixture containing isoeugenol (5 g, 30.5 mmol, 1 eq.), potassium carbonate (6.3 g, 45.7 mmol, 1.5 eq.) and benzyl bromide (4.5 mL, 36.6 mmol, 1.2 eq.) in acetonitrile (80 mL) is refluxed for 12 hours. After cooling to room temperature, the mixture is diluted by adding 100 mL of water and then extracted 3 times with dichloromethane. The organic phases are combined, washed with saturated aqueous NaCl solution and then dried over $Na_2SO_4$ and concentrated. The residue is purified by column chromatography on silica gel (100% hexane) to give benzylated isoeugenol in the form of a white solid (7.4 g, 96% yield).

2nd Step: Dihydroxylation of the Protected Isoeugenol

The benzylated isoeugenol intermediate is added to a solution at 0° C. of oxidizing agent AD-mix-β in a t-BuOH/water mixture (1/1, 400 mL). The reaction medium is stirred vigorously for 24 hours. The excess oxidizing agent is neutralized by adding $Na_2SO_3$ (36 g). After separation of the phases by settling, the organic phase is collected and the aqueous phase is extracted 3 times with ethyl acetate. The organic phases are combined, dried over $Na_2SO_4$ and concentrated. The residue is purified by column chromatography on silica gel ($CH_2Cl_2$/MeOH: 500/4) to give the protected diol intermediate in the form of a colorless oil (7.5 g, 96% yield).

3rd Step: Deprotection of the Intermediate Diol

The protected diol intermediate obtained from the second step (6.46 g, 22.4 mmol) dissolved in methanol (100 mL) is placed in contact with 10% Pd/C catalyst (0.65 g). The reaction mixture is stirred under an atmosphere of dihydrogen at room temperature for 24 hours. The catalyst is removed by filtration and the filtrate is then concentrated under vacuum to give compound 7 in the form of a white powder (4.0 g, 90% yield).

The $^1$H NMR spectra and mass spectra are in accordance with the expected structure.

EXAMPLE 8

Normal human epidermal keratinocytes are seeded at 180 000 cells per well and cultured in SFM culture medium (supplier Gibco) supplemented with 0.25 ng/ml EGF, 25 μg/ml of pituitary extract and 25 μg/ml gentamicin, up to confluence, and incubated in a humid oven at 37° C. and 5% CO2. The culture medium was then replaced with test medium (SFM (Gibco) supplemented with 25 μg/ml gentamicin) containing or not containing (control) the test compounds, or the references (AICAR—(5-amino-4-imidazole carboxamide riboside) at 500 μM). The cells were then incubated for 18 or 48 hours.

The level of expression of p-AMPK was analyzed by Western blotting.

At the end of the incubation, the proteins were extracted and quantified and then separated by electrophoresis on 10% polyacrylamide gel and then transferred onto a nitrocellulose membrane.

After saturation of the membranes in PBS/Tween/1% BSA solution, the phospho-AMPK proteins (Thr-172) (p-AMPK) and GAPDH were successively revealed using specific antibodies that were themselves revealed using an anti-immunoglobulin-peroxidase conjugate. After washing with PBS/Tween, the peroxidase activity and thus the proteins of interest was revealed via the ECL+ (enhanced chemiluminescence) method. Between each successive revelation, the antibodies were detached using a "stripping" buffer. The images were acquired with a Fuji LAS 3000 chemiluminescence scanner (Fujifilm) and the densitometric analyses were performed using the Multigauge software (Fujifilm).

An increase in the phosphorylated form of AMPK (active form of the enzyme) relative to the control is evaluated in this test.

Results

Expressed in the form of the p-AMPK/GAPDH ratio relative to the control (100%):

| Incubation time | Measured ratio | compound | 1 μM | 10 μM | 100 μM | 500 μM |
|---|---|---|---|---|---|---|
| 18 hours | p-AMPK/AMPK | control | | | 100% ± 27% | |
| | | AICAR | — | — | — | 177% ± 31% |
| | | 1 | — | — | 132% ± 11% | |
| 48 hours | p- | control | | 100% ± 7% | | |

| Incubation time | Measured ratio | compound | 1 µM | 10 µM | 100 µM | 500 µM |
|---|---|---|---|---|---|---|
| | AMPK/GAPDH | AICAR | — | — | — | 279 ± 96% |
| | | 5 | 116 ± 17% | 149 ± 25% | 136 ± 14% | — |

EXAMPLE 9

The following anti-aging composition is prepared:
The percentages are indicated on a weight basis.

| | |
|---|---|
| Compound 5 of Example 5 | 1% |
| Glycerol | 12% |
| Polyacrylamide at 40% AM (Sepigel 305 from SEPPIC) | 1% AM |
| Preserving agents | qs |
| Fragrance | qs |
| Water | qs |
| | 100% |

AM: active material

When applied to the skin, this cream reduces the signs of aging of the skin.

The invention claimed is:

1. A process for retarding the onset of and/or reducing the signs of aging of the skin which comprises applying to the skin an effective amount for retarding the onset of and/or reducing the signs of aging of the skin of a composition comprising a physiologically acceptable medium and a compound of formula (I)

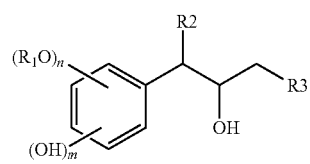

(I)

in which
  n=0; 1; 2 or 3
  m=0; 1; 2 or 3
with $1 \leq m+n \leq 3$
  R1 independently denotes a linear C1-C6 alkyl radical or a branched C3-C6 alkyl radical or a linear C1-C6 acyl radical,
  R2 denotes a hydrogen atom and R3 denotes a hydrogen atom or an OH radical, an optical isomer, stereoisomer and/or diastereoisomer thereof and/or salt thereof
wherein the compound of formula (I) is present at a concentration of between 0.01% and 30% by weight relative to the total weight of the composition.

2. A process for retarding the onset of and/or reducing the signs of aging of the skin which comprises applying to the skin a composition comprising a physiologically acceptable medium and a compound of formula (I)

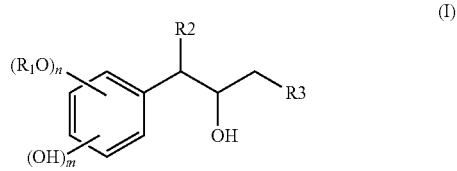

(I)

in which
  n=0; 1; 2 or 3
  m=0; 1; 2 or 3
with $2 \leq m+n \leq 3$
  R1 independently denotes a linear C1-C6 alkyl radical or a branched C3-C6 alkyl radical or a linear C1-C6 acyl radical,
  R2 denotes a hydrogen atom and R3 denotes a hydrogen atom or an OH radical, an optical isomer, stereoisomer and/or diastereoisomer thereof and/or salt thereof
wherein the compound of formula (I) is present at a concentration of between 0.01% and 30% by weight relative to the total weight of the composition.

3. The process as claimed in claim 1, wherein, in the compound of formula (I):

$2 \leq m+n \leq 3$ each of the substituents R1 independently denotes a linear C1-C4 alkyl radical.

4. The process as claimed in claim 1, wherein the compound of formula (I) is a compound of formula (II):

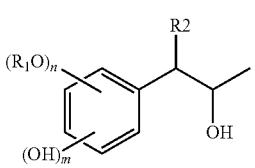

(II)

in which:

$2 \leq m+n \leq 3$.

5. The process as claimed in claim 4, in which:
each of the substituents R1 independently denotes a linear C1-C4 alkyl radical.

6. The process as claimed in claim 1, wherein the compound of formula (I) is chosen from compounds 1 to 4 below, the optical isomers, stereoisomers and diastereoisomers thereof and/or geometrical isomers thereof and/or salts thereof:

| Compound | Structure |
|---|---|
| 1 | HO—⟨benzene⟩—CH₂CH(OH)CH₃, with —O— and HO substituents |
| 2 | dimethoxy-benzene with CH₂CH(OH)CH₃ |
| 3 | trimethoxy-benzene with CH₂CH(OH)CH₃ |
| 4 | methoxy, HO, methoxy benzene with CH₂CH(OH)CH₃ |

7. The process as claimed in claim 1, wherein the compound of formula (I) is a compound of formula (III):

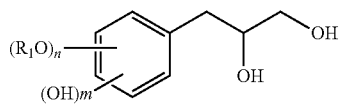

(III)

in which:
n=0; 1; 2 or 3
m=0; 1; 2 or 3
with 1≤m+n≤3
each of the substituents R1 independently denotes a linear C1-C6 alkyl radical or a branched C3-C6 alkyl radical or a linear C2-C6 acyl radical.

8. The process as claimed in claim 1, wherein the compound of formula (I) is chosen from compounds 5 and 6 below, the optical isomers, stereoisomers and diastereoisomers thereof or geometrical isomers thereof and/or salts thereof:

| Compound | Structure |
|---|---|
| 5 | HO—⟨benzene⟩—CH₂CH(OH)CH₂OH with —O— and HO substituents |
| 6 | methoxy, HO, methoxy benzene with CH₂CH(OH)CH₂OH |

9. The process as claimed in claim 1 which is a cosmetic treatment process for retarding the onset of and/or reducing the signs of aging of mature and/or wrinkled skin, characterized in that a compound of formula (I) or a composition containing it, is applied to the mature and/or wrinkled skin.

10. The cosmetic treatment process as claimed in claim 9 which is intended for promoting the renewal of the keratinocytes and for retarding the onset of and/or reducing signs chosen from thinning of the epidermis, surface wrinkles and impairment of the barrier function.

11. The process as claimed in claim 1, wherein the signs on the skin are chosen from wrinkled skin, skin exhibiting impairment of its viscoelastic or biomechanical properties, skin exhibiting impairment in the cohesion of its tissues, thinned skin, and skin exhibiting impairment of its surface appearance.

12. The process as claimed in claim 1, wherein the compound of formula (I) is present, in a composition containing a physiologically acceptable medium, at a concentration of between 0.1% and 10% by weight relative to the total weight of the composition.

13. The process as claimed in claim 1, wherein the compound of formula (I) is present, in a composition containing a physiologically acceptable medium, at a concentration of between 0.5% and 5% by weight relative to the total weight of the composition.

14. The process as claimed in claim 1, wherein the compound of formula (I) is present, in a composition containing a physiologically acceptable medium, wherein the composition does not contain hydrogen peroxide.

* * * * *